United States Patent [19]

Schoenberg et al.

[11] 4,125,494

[45] Nov. 14, 1978

[54] ADHESION PROMOTER FOR 2-CYANOACRYLATE ADHESIVE COMPOSITIONS

[75] Inventors: Jules E. Schoenberg, Scotch Plains; Dilip K. Ray-Chaudhuri, Bridgewater, both of N.J.

[73] Assignee: National Starch and Chemical Corporation, Bridgewater, N.J.

[21] Appl. No.: 823,981

[22] Filed: Aug. 12, 1977

[51] Int. Cl.[2] .................. C07C 121/32; C08L 1/10; C09K 3/00
[52] U.S. Cl. .......................... 260/17 A; 106/287.25; 252/188.3 R; 260/465.4

[58] Field of Search ............... 260/465 Y, 17 A, 881, 260/464, 464.5, 465 D; 106/36, 287; 252/188.3

[56] References Cited

U.S. PATENT DOCUMENTS

| | | | |
|---|---|---|---|
| 2,912,454 | 11/1959 | McKeever | 260/465.4 |
| 3,728,375 | 4/1973 | Coover et al. | 260/465.4 |

Primary Examiner—Theodore Morris
Attorney, Agent, or Firm—James & Franklin

[57] ABSTRACT

Improved 2-cyanoacrylate adhesive compositions containing acetic acid exhibit greatly enhanced bond strength with no significant reduction in cure rate. Such compositions may be used on a wide variety of substrates and are particularly useful on metals.

10 Claims, No Drawings

ADHESION PROMOTER FOR 2-CYANOACRYLATE ADHESIVE COMPOSITIONS

BACKGROUND OF THE INVENTION

I. Field of the Invention

This invention relates to improved 2-cyanoacrylate adhesive compositions having enhanced bond strength. More particularly, this invention is directed to an adhesion promoter for 2-cyanoacrylate adhesive compositions which does not significantly reduce the cure rate thereof.

II. Description of the Prior Art

Adhesive compositions based on 2-cyanoacrylate esters belong to a class of adhesives known as reactive liquid adhesives. 2-Cyanoacrylate adhesives are single-part, low-viscosity adhesives which are characterized by features such as (1) their ability to polymerize at room temperature without the use of an added catalyst when pressed between two substrates, (2) their rapid rate of cure, and (3) the strength of the bonds produced with a wide variety of substrates. Conventional adhesives, on the other hand, cure, for example, upon application of heat and pressure, addition of catalyst, or evaporation of a solvent. A general review of 2-cyanoacrylate adhesives can be found in I. Skeist's "Handbook of Adhesives", New York: Reinhold Publishing Corporation, 1962, Chapter 31, p. 409–414.

Application of the 2-cyanoacrylate adhesive merely involves spreading a small sample thereof in a thin film between two substrates, pressing the substrates together, and allowing the resultant bond to cure. The adhesive develops sufficient strength after a short period of time to hold the substrates together until the adhesive completely polymerizes and builds up to its maximum bonding strength.

Initiation of polymerization, or cure, is generally believed to proceed through an anionic mechanism; the 2-cyanoacrylate adhesives have such a great tendency to polymerize that water itself is a sufficiently active initiator. Hence, when the adhesive is applied to a substrate and thereby exposed to atmospheric and surface moisture, cure normally begins within a relatively short period of time, generally less than one minute, and on many surfaces within a matter of a few seconds. The rapid cure rate of the 2-cyanoacrylate adhesives is particularly advantageous in production line applications.

Due to their tendency to polymerize, the 2-cyanoacrylate adhesive compositions normally contain one or more stabilizers. To prevent anionic polymerization, an inhibitor such as an acidic gas or a protonic acid or anhydride thereof is normally added to the composition. In general, as the acidity of these inhibitors increases, the stability of the adhesive is enhanced while, at the same time, the cure rate is reduced. Free radical polymerization is generally inhibited in the adhesive composition, if necessary, by adding phenolic-type compounds such as hydroquinone or t-butyl catechol thereto. Typical patents which describe the use of these and other compounds as stabilizers for 2-cyanoacrylate adhesive compositions include U.S. Pat. Nos. 2,765,332 and 3,993,678; and Japanese Patent Publication No. 49-31619.

Although adhesive compositions consisting of 2-cyanoacrylate esters and conventional stabilizers inherently yeild high bond strength (as commonly measured by the test of tensile shear strength), improvements therein would be desirable particularly in cases where the substrate is of greater strength than the adhesive, as in the case of many metal bonds. While many stabilizers for 2-cyanoacrylate adhesive compositions have been investigated in the prior art, relatively little research has been done on adhesion promoters which enhance the bond strength of the adhesive without lessening the stability or cure rate thereof. In this regard, selected carboxylic acid anhydrides have been used in the prior art as adhesion promoters for 2-cyanoacrylate adhesive compositions. Thus U.S. Pat. No. 3,832,334 teaches the use of maleic anhydride to increase the bond strength of a 2-cyanoacrylate adhesive at elevated temperatures, while U.S. Pat. No. 3,948,794 teaches the use of itaconic anhydride to improve not only the stability of the 2-cyanoacrylate adhesive composition but also the tensile shear strength and other properties associated therewith.

It has been disclosed in German Offenlegungsschrift No. 26 12 546 that a wide variety of carboxylic acids, generally known to stabilize 2-cyanoacrylate adhesives to varying degrees, exert a definite effect on the bond strength of certain 2-cyanoacrylate adhesive compositions containing excess plasticizer. The plasticizer is added in amounts of 20–60% by weight, based on the total composition, to make the adhesive bonds readily releasable. It is suggested that one of the functions of the carboxylic acid therein is to counteract the weakening effect of the plasticizer on the bond strength of the adhesive. Nevertheless, the large number of carboxylic acids described as being applicable in the German publication limits the use of the adhesive composition to very few types of substrates. For example, many of the carboxylic acids listed therein, i.e., those with a high acid strength (low $pK_a$), act very effectively as anionic polymerization inhibitors and hence will significantly retard the rate of cure of the adhesive, particularly on non-polar substrates, within the concentration range given therein. Yet, as described hereinabove, the rapid rate of cure is one of the main characterizing features of 2-cyanoacrylate adhesives in general. Furthermore, it has been demonstrated that at least some of the weaker acids (with relatively high $pK_a$) within the scope of the German publication, which acids do not significantly reduce the rate of cure of the adhesive composition, have in fact very minimal effect on the bond strength of the composition on many metals.

Accordingly, it is an object of the present invention to provide an improved 2-cyanoacrylate adhesive having enhanced bond strength.

It is another object to provide an adhesion promoter for 2-cyanoacrylate adhesive compositions which does not significantly reduce the cure rate thereof.

It is a further object to provide a process for improving the adhesive properties of a fully stabilized 2-cyanoacrylate adhesive composition.

SUMMARY OF THE INVENTION

The above and related objects are achieved in preparing an improved adhesive composition comprising a mixture of:

(A) a fully stabilized 2-cyanoacrylate adhesive consisting essentially of:

(1) a monomeric ester of 2-cyanoacrylic acid of the general formula:

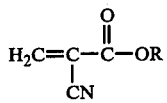

wherein R is an alkyl or alkenyl group having from 1 to 16 carbon atoms, a cyclohexyl group or a phenyl group, and (2) an effective amount of an anionic polymerization inhibitor selected from the group consisting of acidic gases, protonic acids and anhydrides thereof, wherein said anionic polymerization inhibitor has a $pK_a$ less than about 4; and (B) from 0.02 to 0.3% by weight, based on the total composition, of acetic acid, said composition being characterized by a tensile shear strength of at least 80 kg./cm.$^2$ as measured on brass.

The process for preparing such an improved adhesive composition comprises the step of dissolving the specified amount of acetic acid into the fully stabilized 2-cyanoacrylate adhesive described hereinabove.

If the adhesive composition is to be stored for an extended period of time, it may be desirable to add a free radical polymerization inhibitor to the composition of this invention for added storage stability. In addition, other optional ingredients which improve specific properties of the adhesive such as thickeners or plasticizers may be incorporated into the composition.

Acetic acid is a known, albeit weak, stabilizer for 2-cyanoacrylate adhesive compositions as disclosed in U.S. Pat. Nos. 2,912,454 and 2,926,188. However, it is believed that the ability of acetic acid to promote the adhesive of a fully stabilizer 2-cyanoacrylate adhesive composition has heretofore not been recognized. Of the many carboxylic acids which are potentially capable of enhancing the bond strengths of 2-cyanoacrylate adhesives, only the weak acids with $pK_a$ greater than about 4, employed within a certain concentration range, do not significantly retard the rate of cure of conventional 2-cyanoacrylate adhesives when applied to non-polar substrates. Of these weak acids, only acetic acid serves to enhance the bond strength of the adhesive composition when applied to many substrates which are stronger than the adhesive bond, such as most metal substrates. It is necessary that the acetic acid employed in the composition be within a specified concentration, and only the narrow range given hereinabove is effective in obtaining the high bond strengths characteristic of this invention. In a preferred embodiment, 0.03–0.1% by weight of acetic acid is employed.

DESCRIPTION OF THE PREFERRED EMBODIMENTS

The adhesive composition of the present invention is based on a monomeric ester or mixture of esters of 2-cyanoacrylic acid as described hereinabove. For purposes of this invention, the preferred esters are those wherein the R group is an alkyl or alkenyl group having 1 to 4 carbon atoms, and more particularly, a methyl, ethyl, butyl, isobutyl, or allyl group. An especially preferred ester for preparing the adhesives of this invention is ethyl 2-cyanoacrylate.

The above-mentioned monomeric esters of 2-cyanoacrylic acid may be prepared by methods well known in the art such as those described in U.S. Pat. Nos. 2,467,926; 2,467,927; and 3,254,111; the disclosures of which are incorporated herein by reference.

The 2-cyanoacrylate esters are stabilized by adding one or more known anionic polymerization inhibitors thereto. The inhibitor employed must have a $pK_a$ of less than about 4 to be effective in fully stabilizing the ester and, in addition, must be an acidic gas, protonic acid or anhydride thereof. The term anhydrides, as used herein, refers to compounds which react rapidly with water to produce protonic acids having pH less than 4. Hence, a wide variety of anionic polymerization inhibitors known in the art to stabilize 2-cyanoacrylate adhesive compositions is applicable herein. Examples of suitable acidic gases include sulfur dioxide, nitric oxide, hydrogen fluoride, and the like. Suitable protonic acids include mineral acids such as, for example, hydrochloric, sulfuric or phosphoric acids and organic acids with $pK_a$ less than 4 such as, for example, sulfonic or carboxylic acids. Examples of anhydrides of protonic acids which are applicable include carboxylic acid anhydrides, phosphoric acid anhydrides such as phosphorus pentoxide, sultones, acid chlorides, and the like. The preferred anionic polymerization inhibitor to be employed herein is sulfur dioxide.

Those anionic polymerization inhibitors which are in the gaseous form act not only to lengthen the shelf life of the adhesive but also are used as process stabilizers. Hence, throughout several stages in the synthesis of the 2-cyanoacrylate ester, the gaseous inhibitor, such as, for example, sulfur dioxide, is passed through the system. The high concentration of inhibitor which is thus built up is removed by pulling vacuum on the ester upon completion of the synthesis procedure. This process of stabilizing the adhesive during synthesis is known and is typically described in U.S. Pat. No. 2,756,251.

The anionic polymerization inhibitor must be employed in an amount effective to fully stabilize the 2-cyanoacrylate ester. The concentration range of inhibitor typically used to effectively stabilize the ester is 0.001–0.5% by weight, based on the total composition; however, because the amount of stabilizer depends on many factors, it may be required in certain instances to use amounts outside of this range. Furthermore, it may not always be necessary to add an anionic polymerization inhibitor if the 2-cyanoacrylate ester used in the composition is commercially obtained because the commercially produced esters in some cases already contain an effective amount of inhibitor for stabilization purposes.

To improve the adhesive properties of the 2-cyanoacrylate adhesive composition fully stabilized with anionic polymerization inhibitor, acetic acid is added thereto as the novel feature of this invention. As stated hereinabove, acetic acid, unlike strong acids, will not significantly retard the cure rate of the adhesive composition on non-polar surfaces at the concentration levels used herein. The adhesion-promoting ability of acetic acid is observed when many substrates which are stronger than the adhesive bond, such as most metals, are bonded. In addition to metals, other substrates generally known to be bondable by means of 2-cyanoacrylate adhesives, such substrates including, for example, rubber, most plastics, phenolic resins, glass, and the like, may also be bonded using the adhesive composition of this invention. However, for certain of these substrates wherein the adhesive bond is stronger than the substrate itself, enhancement of the bond strength will not be observed.

The amount of acetic acid to be used depends on the surface to which the composition is applied but is generally in the range of from 0.02 to 0.3% by weight, based on the total weight of the composition, sufficient to give a tensile gear strength of at least 80 kg./cm.$^2$ as measured on brass. At a concentration of acetic acid not much above 0.3%, the bond strength of the adhesive composition is decreased relative to a control and the cure rate is noticably retarded. To optimize both bond strength and cure rate the preferred range of acetic acid to be employed in the adhesive composition for most substrates is 0.03–0.1% by weight.

For added storage stability it may be desirable to add a free radical polymerization inhibitor to the composition. Specifically, if the adhesive composition is to be used shortly after it is prepared, no free radical polymerization inhibitor is necessary; however, if the composition is to be stored for prolonged periods of time, addition of such an inhibitor for stabilization purposes is highly recommended. As a suitable inhibitor for this purpose, any one of a wide variety of inhibitors known in the art to stabilize 2-cyanoacrylate adhesive compositions against free radical polymerization is applicable. Such inhibitors include phenolic compounds such as hydroquinone, t-butyl catechol, pyrocatechol, p-methoxyphenol, and the like. The conventional free radical polymerization inhibitor, like the anionic polymerization inhibitor, is normally added during the processing of the 2-cyanoacrylate ester. Hence, a free radical polymerization inhibitor is generally introduced into the distillation vessel and the receiver to stabilize the ester in the synthesis thereof. As a result, commercially available 2-cyanoacrylate esters may already contain a certain amount of a conventional free radical polymerization inhibitor such as those mentioned hereinabove. More such inhibitor, however, may be added thereto if greater stability is desired. The total amount of such inhibitor which will be effective for stabilization purposes will range from 0.001 to 0.05% by weight of the total composition.

There may also be present in the adhesive compositions of this invention various other optional ingredients including, for example, plasticizers and thickeners. Plasticizers improve the aging characteristics of the cured bonds by lessening the brittleness thereof. The best performance the amount of plasticizer to be used should not exceed 20% by weight of the total composition. Suitable platicizers include monofunctional and difunctional aliphatic esters of acids having 1 to 10 carbon atoms such as, for example, dimethyl octyl sebacate and esters of malonic acid, difunctional aromatic esters, phosphates and phosphonates. Thickeners, which may be used in amounts of up to 25% by weight, depending in part on their degree of fluidity at room temperature, serve to increase the viscosity of the adhesives so that they may be more easily applied. Among the suitable thickeners for this purpose are included, for example, polymeric alkyl 2-cyanoacrylates, cellulose esters including cellulose acetate butyrate, acrylate resins such as poly(methyl methacrylate) and poly(ethyl methacrylate), and poly(vinyl alkyl ethers) such as poly(vinyl methyl ether).

The adhesive compositions of the present invention are generally prepared by adding a given amount of acetic acid to the stabilized 2-cyanoacrylate ester and mixing at room temperature until the acetic acid is thoroughly dissolved in the ester. The anionic polymerization inhibitor is already present in or added to the ester before the acetic acid is dissolved therein. Any optional ingredients desired, including the free radical polymerization inhibitor, may be added either prior to or following the addition of acetic acid. The resultant adhesive composition may be used in a variety of applications, including household articles, precision instruments, optical lenses, and the like.

The following examples will demonstrate the efficacy of the 2-cyanoacrylate adhesive compositions of this invention. In these examples all percentages are given by weight unless othewise specified.

The present adhesive compositions are evaluated on the basis of the following two test procedures:

I. SET TIME TEST

One drop of test adhesive is placed near one edge of a 2.54 cm. by 2.54 cm. by 0.48 cm. phenolic chip. The mating surface of a second chip of the same dimensions is quickly placed thereover and positioned such that half of each chip overlaps the other chip. The lamination is immediately clamped together by means of a spring clip. At 15 second intervals an attempt is made to pull the two chips apart using a light peel force. For those samples which bond within the first 15 second interval, the test is repeated at 5 second intervals. The "set time" is related to the cure rate and is defined as the time interval between the initial application of the adhesive and the final time at which the chips can no longer be pulled apart manually.

II. TENSILE SHEAR STRENGTH TEST

Two metal bars of dimensions 1.27 cm. by 10.16 cm. by 0.32 cm. are used as the test materials to be bonded. Prior to use, they are treated by scouring with Scotch-Brite (Registered Trademark of 3 M Co.) scouring pads and then cleaned with acetone.

A small amount (10 microliters) of test adhesive is applied to the cleaned surface of one bar near one edge. The second bar is then pressed against the first to form an adhesive film such that there is 1.27 cm. overlap for each bar and hence a bonding area of 1.61 cm.$^2$. The bars are clamped together by means of a spring clip and allowed to cure for 24 hours. The bond strength, or tensile shear strength, is determined by pulling the bars apart with an Instron Tensile Tester at a crosshead operation speed of 0.254 cm./min. The values given herein for the tensile shear strength are usually the average of five determinations and are given in units of kg./cm.$^2$.

EXAMPLE I

This example illustrates the effect of carboxylic acids of varying strength on the cure rate of 2-cyanoacrylate adhesive compositions.

Eight samples of 2-cyanoacrylate adhesive compositions were prepared by dissolving approximately equal amounts of a given carboxylic acid in a quantity of ethyl 2-cyanoacrylate obtained commercially containing 0.002% sulfur dioxide and 0.0075% hydroquinone as stabilizers. Each resulting composition was evaluated against a control containing no acid as to set time on phenolic chips. The results are given in Table I.

TABLE I

| Carboxylic Acid | pK$_a$ of Acid | Amount of Acid Added meq./kg.* | Amount of Acid Added % by weight | Set Time (seconds) |
|---|---|---|---|---|
| None (control) | — | 0 | 0 | 5 |
| Propionic | 4.9 | 7.8 | 0.058 | 5 |
| iso-Butyric | 4.8 | 8.3 | 0.073 | 10 |

TABLE I-continued

| Carboxylic Acid | pK$_a$ of Acid | Amount of Acid Added meq./kg.* | Amount of Acid Added % by weight | Set Time (seconds) |
|---|---|---|---|---|
| Acetic | 4.8 | 8.2 | 0.049 | 5 |
| Benzoic | 4.2 | 8.2 | 0.10 | 15 |
| Formic | 3.8 | 8.0 | 0.37 | 15 |
| Salicylic | 3.0 | 8.7 | 0.12 | 30 |
| Malonic | 2.8 | 8.5 | 0.044 | 60 |
| Cyanoacetic | 2.5 | 8.3 | 0.071 | 45 |

*Milliequivalents per kilogram. The numbers in this column indicate that comparable amounts of each carboxylic acid were used on an equivalent basis. (Equivalency is based on the number of acidic protons per molecule.)

From Table I it is evident that the weak acids such as acetic, propionic and iso-butyric acids have a minimal effect on the cure rate of the adhesive composition. In contrast, the stronger acids with pK$_a$ less than about 4 act more effectively as anionic polymerization inhibitors and hence cause significant retardation in the rate of cure, the retardation being generally more pronounced as the acid strength increases.

EXAMPLE II

This example illustrates the unique adhesion-promoting ability of acetic acid in 2-cyanoacrylate adhesive compositions.

Three samples of 2-cyanoacrylate adhesive compositions were prepared by dissolving the given amount of either acetic, propionic or iso-butyric acid in a quantity of ethyl 2-cyanoacrylate obtained commercially containing 0.0023% sulfur dioxide and 0.01% hydroquinone as stabilizers. Each resulting composition was evaluated against a control as to tensile shear strength. The resuls are given in Table II.

TABLE II

| Carboxylic Acid | Amount of Acid Added meq./kg. | Amount of Acid Added % by weight | Tensile Shear Strength (kg./cm.$^2$) Steel | Tensile Shear Strength (kg./cm.$^2$) Brass | Tensile Shear Strength (kg./cm.$^2$) Aluminum |
|---|---|---|---|---|---|
| None (control) | 0 | 0 | 80 | 75 | 70 |
| Propionic | 5.8 | 0.043 | 113 | 58 | 65 |
| iso-Butyric | 5.2 | 0.046 | 63 | 42 | 82 |
| Acetic | 5.3 | 0.032 | 134 | 84 | 96 |

Acetic acid is the only weak carboxylic acid which increases the bond strength of the 2-cyanoacrylate adhesive on all three types of metal substrates. Its unique role as an adhesion promoter which does not adversely affect the cure rate of the adhesive distinguishes acetic acid from other carboxylic acids and renders it a particularly desirable additive for 2-cyanoacrylate adhesive compositions.

EXAMPLE III

This example illustrates the effect of acetic acid concentration on the bond strength of the adhesive compositions of this invention.

The 2-cyanoacrylate adhesive compositions were prepared by dissolving the given amount of acetic acid in ethyl 2-cyanoacrylate obtained commercially containing 0.0028% sulfur dioxide and 0.001% hydroquinone as stabilizers. The resulting compositions were evaluated against a control as to tensile shear strength. The results are given in Table III.

TABLE III

| Amount of Acetic Acid (% by weight) | Tensile Shear Strength (kg./cm.$^2$) Steel | Tensile Shear Strength (kg./cm.$^2$) Brass | Tensile Shear Strength (kg./cm.$^2$) Aluminum |
|---|---|---|---|
| None (control) | 134 | 104 | 111 |
| 0.005 | 117 | 102 | 98 |
| 0.01 | 108 | 106 | 89 |
| 0.02 | 142 | 120 | 103 |
| 0.04 | 167 | 169 | 136 |
| 0.10 | 242 | 176 | 158 |
| 0.21 | 212 | 131 | 171 |
| 0.29 | 143 | 122 | 75 |
| 0.41 | 97 | 63 | 64 |
| 0.50 | 77 | 40 | 61 |

The results indicate that only a certain concentration range of acetic acid (about 0.02 to 0.3% by weight) is effective in enhancing the bond strength of the adhesive composition. Because of the reduction in set time at high concentrations of acetic acid, however, the preferred range is 0.03–0.1% to maintain optimum values for both bond strength and cure rate.

EXAMPLE IV

This example illusrates the use of acetic acid in adhesive compositions based on three different 2-cyanoacrylate esters.

Three samples of adhesive composition were prepared by dissolving 0.05% by weight of acetic acid in either methyl, n-butyl or allyl 2-cyanoacrylate, each containing a fixed amount of sulfur dioxide and hydroquinone as stabilizers. As controls, methyl, n-butyl and allyl 2-cyanoacrylate stabilized as above without any acetic acid incorporated therein were employed. The resulting six compositions were subjected to the tensile shear strength test. The results are given in Table IV.

TABLE IV

| 2-Cyanoacrylate Ester | Adhesion Promoter | Tensile Shear Strength (kg./cm.$^2$) Steel | Tensile Shear Strength (kg./cm.$^2$) Brass | Tensile Shear Strength (kg./cm.$^2$) Aluminum |
|---|---|---|---|---|
| Methyl | None (control) | 179 | 180 | 166 |
| Methyl | Acetic Acid | 177 | 214 | 171 |
| n-Butyl | None (control) | 63 | 64 | 55 |
| n-Butyl | Acetic Acid | 118 | 108 | 86 |
| Allyl | None (control) | 87 | 90 | 69 |
| Allyl | Acetic Acid | 131 | 113 | 90 |

In nearly all cases, the acetic acid acted to enhance the bond strength of the adhesive composition relative to the control.

Summarizing, this invention is seen to provide an improved 2-cyanoacrylate adhesive composition characterized by both enhanced bond strength and no significant reduction in cure rate by the addition of a small amount of acetic acid to a fully stabilized 2-cyanoacrylate adhesive.

Now that the preferred embodiments of the present invention have been described in detail, various modifications and improvements thereon will become readily apparent to those skilled in the art. Accordingly, the spirit and scope of the invention are to be limited only by the appended claims, and not by the foregoing specification.

What is claimed is:

1. An improved adhesive composition comprising a mixture of:
   (A) a fully stabilized 2-cyanoacrylate adhesive consisting essentially of:
      (1) a monomeric ester of 2-cyanoacrylic acid of the general formula:

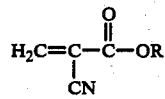

wherein R is an alkyl or alkenyl group having from 1 to 16 carbon atoms, a cyclohexyl group or a phenyl group, and (2) an effective amount of an anionic polymerization inhibitor selected from the group consisting of acidic gases, protonic acids and anhydrides thereof, wherein said anionic polymerization inhibitor has a $pK_a$ less than about 4; and (B) an amount of acetic acid, in the range of from 0.02 to 0.3% by weight, based on the total composition, sufficient to provide said composition with a tensile shear strength of at least 80 kg./cm.$^2$ as measured on brass.

2. The adhesive composition of claim 1 wherein said acetic acid is present in an amount of 0.03–0.1% by weight.

3. The adhesive composition of claim 2 wherein R is an ethyl group.

4. The adhesive composition of claim 1 wherein R is an alkyl or alkenyl group having from 1 to 4 carbon atoms.

5. The adhesive composition of claim 4 wherein R is an ethyl, allyl, methyl or n-butyl group.

6. The adhesive composition of claim 1 wherein said anionic polymerization inhibitor is sulfur dioxide.

7. The adhesive composition of claim 1 wherein there is additionally present a free radical polymerization inhibitor.

8. The adhesive composition of claim 1 wherein said composition contains a thickener.

9. The adhesive composition of claim 1 wherein said composition contains up to 20% by weight of a plasticizer, based on the total composition.

10. A process for improving the adhesive properties of a fully stabilized 2-cyanoacrylate adhesive composition which composition consists essentially of:

(A) a monomeric ester of 2-cyanoacrylic acid of the general formula:

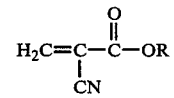

wherein R is an alkyl or alkenyl group having from 1 to 16 carbon atoms, a cyclohexyl group or a phenyl group, and (B) an effective amount of an anionic polymerization inhibitor selected from the group consisting of acidic gases, protonic acids, and anhydrides thereof, wherein said anionic polymerization inhibitor has a $pK_a$ of less than about 4, said process comprising the step of dissolving into said composition from 0.02 to 0.3% by weight, based on the total composition, of acetic acid sufficient to provide a tensile shear strength of at least 80 kg./cm.$^2$ as measured on brass.

* * * * *